(12) United States Patent
Mahler et al.

(10) Patent No.: US 11,246,342 B2
(45) Date of Patent: Feb. 15, 2022

(54) EXTRACTOR FOR AN AEROSOL-GENERATING DEVICE

(71) Applicant: Philip Morris Products S.A., Neuchatel (CH)

(72) Inventors: Boris Mahler, Chamblon (CH); Dani Ruscio, Cressier (CH); Olivier Greim, Yverdon-les-Bains (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/546,315

(22) PCT Filed: Feb. 1, 2016

(86) PCT No.: PCT/EP2016/052088
§ 371 (c)(1),
(2) Date: Jul. 26, 2017

(87) PCT Pub. No.: WO2016/124550
PCT Pub. Date: Aug. 11, 2016

(65) Prior Publication Data
US 2018/0049472 A1     Feb. 22, 2018

(30) Foreign Application Priority Data

Feb. 6, 2015   (EP) .................................... 15154218

(51) Int. Cl.
*A24F 40/20*     (2020.01)
*A24F 40/40*     (2020.01)
(Continued)

(52) U.S. Cl.
CPC .............. *A24F 40/40* (2020.01); *A24F 40/42* (2020.01); *A24F 40/46* (2020.01);
(Continued)

(58) Field of Classification Search
CPC .... A24F 13/08; A24F 7/00; A24F 7/06; A24F 13/06; A24F 40/20; A24F 40/40;
(Continued)

(56) References Cited

U.S. PATENT DOCUMENTS

| 1,527,991 A |   | 3/1925 | Murphy |
|---|---|---|---|
| 4,461,308 A | * | 7/1984 | Le Cover ............... A24D 3/045 131/198.1 |

(Continued)

FOREIGN PATENT DOCUMENTS

| CN | 103997922 A | 8/2014 |
|---|---|---|
| CN | 104135881 A | 11/2014 |

(Continued)

OTHER PUBLICATIONS

Office Action dated Oct. 22, 2018 in Japanese Patent Application No. 2017-541607, with English translation, 12 pages.

(Continued)

*Primary Examiner* — Alex B Efta
(74) *Attorney, Agent, or Firm* — Oblon, McClelland, Maier & Neustadt, L.L.P.

(57) ABSTRACT

An elongated aerosol-generating device configured to receive an aerosol-generating article is provided, including a heater extending longitudinally with respect to the device, being configured to heat the article and to penetrate an internal portion thereof; and an extractor configured to extract the article received in the device, being movably coupled to the device between operating and extraction positions, the operating position defined by the heater contacting the article, and the extraction position defined by the heater separated from the article, the extractor including a cavity to receive the article, a first aperture through an end-wall of the cavity and being configured to allow the heater to penetrate the cavity when the extractor is moved (Continued)

between the extraction and operating positions, wherein the extractor further defines an air-flow channel to allow air flow into the cavity, an inlet of the channel being positioned radially-outward of the first aperture.

8 Claims, 5 Drawing Sheets

(51) Int. Cl.
  *A24F 40/42*   (2020.01)
  *A61M 15/00*   (2006.01)
  *A61M 15/06*   (2006.01)
  *A24F 40/46*   (2020.01)

(52) U.S. Cl.
  CPC ........ *A61M 15/0023* (2014.02); *A61M 15/06* (2013.01); *A24F 40/20* (2020.01); *A61M 15/0091* (2013.01); *A61M 2205/3331* (2013.01)

(58) Field of Classification Search
  CPC ... A24F 40/46; A61M 15/06; A61M 15/0023; A61M 15/0091
  See application file for complete search history.

(56) References Cited

U.S. PATENT DOCUMENTS

| | | | | |
|---|---|---|---|---|
| 4,947,874 A * | 8/1990 | Brooks | ................ | A24F 47/008 131/329 |
| 5,144,962 A | 9/1992 | Counts et al. | | |
| 5,240,012 A | 8/1993 | Ehrman et al. | | |
| 5,388,594 A * | 2/1995 | Counts | ................ | H05B 3/42 131/329 |
| 5,878,752 A * | 3/1999 | Adams | ................ | A24F 47/008 131/329 |
| 5,954,979 A * | 9/1999 | Counts | ................ | A24F 47/008 131/194 |
| 2011/0094523 A1 | 4/2011 | Thorens et al. | | |
| 2015/0013696 A1 | 1/2015 | Plojoux et al. | | |

FOREIGN PATENT DOCUMENTS

| | | |
|---|---|---|
| EP | 2 319 334 A1 | 5/2011 |
| JP | 62-119948 | 7/1987 |
| JP | 11-164679 | 6/1999 |
| JP | 2014-533513 | 12/2014 |
| KR | 10-2014-0093694 A | 7/2014 |
| KR | 10-2014-0123487 A | 10/2014 |
| WO | WO 2013/098395 | 4/2013 |
| WO | WO 2013/076098 A2 | 5/2013 |
| WO | WO 2013/102609 A2 | 7/2013 |
| WO | WO-2013102609 A3 * | 4/2014 .......... A24F 47/008 |
| WO | WO 2014/118286 A2 | 8/2014 |
| WO | 2015/197627 A1 | 12/2015 |

OTHER PUBLICATIONS

International Preliminary Report on Patentability and Written Opinion dated Aug. 17, 2017 in PCT/EP2016/052088.
Office Action dated Feb. 19, 2018 in Japanese Patent Application No. 2017-541607 (submitting English translation only), 5 pages.
Korean Office Action dated Apr. 6, 2018 in Patent Application No. 10-2017-7019809 (submitting English translation only), 7 pages.
International Search Report and Written Opinion dated Apr. 18, 2016 in PCT/EP2016/052088, filed Feb. 1, 2016.
Japanese Decision to Grant with English translation dated Jul. 1, 2019 in corresponding Japanese Patent Application No. 2017-541607, (4 pages).
Combined Office Action and Search Report dated Aug. 28, 2019 in Chinese Patent Application No. 201680007197.9, 18 pages (with English translation).
Extended European Search Report dated Mar. 15, 2021 in corresponding European Patent Application No. 20207982.8, 8 pages.

* cited by examiner

EXTRACTOR FOR AN AEROSOL-GENERATING DEVICE

The present specification relates to an elongated aerosol-generating device for use with an aerosol-generating article comprising an aerosol-forming substrate. The aerosol-generating article can be received by the aerosol-generating device. The device includes an extractor for assisting the removal of the aerosol-generating article after consumption.

A number of prior art documents disclose aerosol-generating devices that include, for example, heated smoking systems and electrically heated smoking systems. One advantage of these systems is that they significantly reduce sidestream smoke, while permitting the smoker to selectively suspend and reinitiate smoking. An example of a heated smoking system is disclosed in U.S. Pat. No. 5,144,962, which includes in one embodiment a flavour-generating medium in contact with a heater. When the medium is exhausted, both it and the heater are replaced. An aerosol-generating device where a substrate can be replaced without the need to remove the heating element is desirable.

WO2013/076098 provides a disclosure of an aerosol-generating device having a heater that is insertable into the aerosol-forming substrate of an aerosol-generating article and an extractor for facilitating the removal of the aerosol-generating article after use. Although the extractor of WO2013/076098 is successful in maintaining integrity of an aerosol-generating article during removal, a problem has been identified. Loose fragments of aerosol-forming substrate and other debris derived from the aerosol-generating article tend to fall out of the extractor and accumulate in the aerosol-generating device. This may adversely affect the air-flow path that allows air to pass over the aerosol-forming substrate as it is difficult to clean the region of the device around the base of the heater efficiently.

The present disclosure relates to an elongated aerosol-generating device capable of receiving an aerosol-generating article. The aerosol-generating device comprises a heater for heating the aerosol-generating article and an extractor for extracting an aerosol-forming article received in the aerosol-generating device. The heater extends longitudinally with respect to the elongated aerosol-generating device and is configured for penetrating an internal portion of the aerosol-generating article. The extractor is movably coupled to the aerosol-generating device between a first position and a second position, the first position being an operating position defined by the heater being in contact with the aerosol-generating article, and the second position being an extraction position defined by the heater being separated from the aerosol-generating article. The extractor comprises a cavity for receiving the aerosol-generating article. A first aperture is defined through an end-wall of the cavity for allowing the heater to penetrate the cavity when the extractor is moved between the second position and the first position. The extractor further defines an air-flow channel for allowing air flow into the cavity, an inlet of the air-flow channel being positioned at a point that is radially-outward of the first aperture.

In use, a user draws on an end of an aerosol-generating article received in the cavity. The aerosol-generating article comprises an aerosol-forming substrate that is heated by the heater. Air is drawn into the cavity through the air-flow channel and flows over the aerosol-forming substrate. Volatile components evolved from the heated aerosol-forming substrate are entrained into the air-flow and condense, forming an inhalable aerosol.

In the aerosol-generating device disclosed in WO2013/076098 air flows into the extractor cavity through the same aperture that allows the heater to penetrate into the cavity. An air flow path within the device allows air to reach an underside of the end-wall of the cavity and from there the air flows through the aperture, along side the heater and into the cavity. The need for air to flow through the cavity means that the aperture needs to be dimensioned such that there is sufficient clearance to allow the desired air flow once the heater is in position. After a number of uses, debris from successive aerosol-generating articles falls through the aperture and collects around the base of the heater and in the air flow path of the device. This debris may be adherent and may build up to obstruct or block the air-flow path through the device, thereby inhibiting the consumer's experience. It is difficult to clean debris that builds up in the device outside the cavity of the extractor.

In the present disclosure the first aperture, for accommodating the heater, is not the air inlet position into the extractor. The air inlet is spaced radially outside the first aperture. Preferably the air inlets are defined in a side wall of the extractor or through a side portion of the end-wall of the extractor. For example, an inlet of the air-flow channel may be defined in a radially-outermost portion of the end-wall. At least a portion of the air-flow channel may extend radially within the end-wall, that is, between internal and external surfaces of the end-wall.

Preferably the air-flow path through the extractor involves air flowing in a radial direction towards the heater for at least a portion of the air-flow path. Debris falling through the first aperture will, therefore, not block the air-flow path. It may be that debris blocks the air-flow path internally, but it is preferred that the extractor can be removed from the device to allow any such debris to be easily removed, for example by washing with water.

Preferably, the first aperture is dimensioned to allow a clearance of 0.5 mm or less to the heater. The clearance of 0.5 mm or less allows a portion of the heater to pass through the aperture, so as to enter the cavity and penetrate an aerosol-forming article within the cavity, but helps to prevent the egress of particles of aerosol-forming substrate or other debris from the cavity. It may be preferable that the first aperture has dimensions identical to cross-sectional dimensions of the heater so that the heater scrapes the aperture when passing into and out of the cavity. This may further prevent egress of debris from the cavity through the first aperture.

The air-flow path from the air-flow channel inlet may join with the first aperture.

The extractor is preferably designed such that particles of aerosol-forming substrate, or other debris that may derive from an aerosol-generating article, is trapped or retained within the extractor portion of the aerosol-generating device when the aerosol-generating article has been extracted. The extractor may then be removed from the device and cleaned on a regular basis to maintain the consumer experience.

In preferred embodiments, an outer face of the end-wall may abut a portion or face of the aerosol-generating device when the extractor is in the first position, such that debris from the aerosol-generating article cannot build up in the aerosol-generating device. That is, there is no gap for debris to fall into between the extractor and the remaining parts of the aerosol-generating device. This may help ensure that any debris is retained within the extractor.

The extractor may comprise a first air-flow channel and a second air-flow channel, inlets to the first and second air-flow channels being located on opposite sides of the extractor. There may be more than two air-flow channels.

Air may flow into the cavity via outlets from the air-flow channels that are defined in an internal surface of the end-wall. Air may flow into the cavity via outlets from the air-flow channels that join the first aperture, such that air flow into the cavity is directed over or near the heater.

The disclosure may also relate to an aerosol-generating system comprising an elongated aerosol-generating device as described above and an aerosol-generating article, the aerosol-generating article comprising an aerosol-forming substrate for evolving an inhalable aerosol when heated by the heater. The aerosol-forming substrate may comprise a sheet of homogenised tobacco.

When an aerosol-forming article is received within the cavity of the extractor, the extractor may be capable of positioning the aerosol-forming substrate in contact with the heater.

As used herein, the term 'positioning' relates to the movement of the aerosol-generating article or the aerosol-forming substrate relative to the heater of the aerosol-generating device. Thus, the extractor can be said to be capable of moving the aerosol-forming substrate relative to the heater in order to facilitate the removal of the aerosol-forming substrate from the aerosol-generating device.

As used herein, an 'aerosol-generating device' relates to a device that interacts with an aerosol-forming substrate of an aerosol-generating article to generate an aerosol. The aerosol-forming substrate is part of an aerosol-generating article, for example part of a smoking article. An aerosol-generating device may comprise one or more components used to supply energy from a power supply to an aerosol-forming substrate to generate an aerosol. For example, an aerosol-generating device may be a heated aerosol-generating device. An aerosol-generating device may be an electrically heated aerosol-generating device or a gas-heated aerosol-generating device. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder for an aerosol-generating article.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' and 'smoking article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. The term 'smoking article' is generally used hereafter.

Preferably a smoking article is a heated smoking article, which is a smoking article comprising an aerosol-forming substrate that is intended to be heated rather than combusted in order to release volatile compounds that can form an aerosol. The aerosol formed by heating the aerosol-forming substrate may contain fewer known harmful constituents than would be produced by combustion or pyrolytic degradation of the aerosol-forming substrate. A smoking article may be, or may comprise, a tobacco stick.

In one embodiment, the extractor positions the smoking article comprising an aerosol-forming substrate in a first position and a second position, the first position being an operating position defined by the heater being in contact with the aerosol-forming substrate, and the second position being an extraction position defined by the aerosol-forming substrate being separated from the heater. Thus, the extractor may be movably coupled to an aerosol-generating device, and may be movable between a first position in which the aerosol-forming substrate is in contact with a heater of the aerosol-generating device, and a second position in which the aerosol-forming substrate is separated from the heater. Preferably the extractor remains coupled to the aerosol-generating device when in the first position, the second position and any intermediate point between the first position and second position. The extractor may be removably coupleable to the aerosol-generating device, in which case when the extractor is removed from the device it is neither in the first position nor the second position.

The extractor may be slidable between the first position and the second position.

The first position of the extractor is an operating position in which the heater can heat the aerosol-forming substrate of the smoking article to form the aerosol. As known to those of ordinary skill in the art, an aerosol is a suspension of solid particles or liquid droplets or both solid particles and liquid droplets in a gas, such as air. The second position of the extractor is an extraction position which facilitates removal of the smoking article from the aerosol-generating device. The upstream and downstream ends of the aerosol-generating article are defined with respect to the airflow when the user takes a puff. Typically, incoming air enters the aerosol-generating article at the upstream end, combines with the aerosol, and carries the aerosol in the airflow towards the user's mouth at the downstream end.

The extractor allows the integrity of the aerosol-forming substrate to be substantially maintained as the smoking article is removed from the aerosol-generating device.

The aerosol-generating device may further comprise a stopper for preventing the extractor from sliding out of the aerosol-generating device when the extractor is moved to the second position. The stopper may be arranged to cooperate with stopper receiving means, for example an indent or depression for receiving the stopper. The stopper may be provided on the extractor. The stopper receiving means may be provided on another part of the aerosol-generating device.

The aerosol-generating device may further comprise a guide pin for guiding the extractor as the extractor is moved between the first and second positions. The guide pin substantially prevents the extractor from rotating relative to the aerosol-generating device. The guide pin may be arranged to cooperate with a slot or groove. The guide pin, for example, may be provided on the extractor. The slot or groove may be provided in another part of the aerosol-generating device.

The extractor may comprise insulating material, for providing insulation from the heat of the heater.

The aerosol-generating device may be an electrically heated smoking system comprising an electric heater. In other embodiments the aerosol-generating device may be a heater smoking system comprising a gas-burner, or some source of heat other than electricity. The term "electric heater" refers to one or more electric heating elements. The electric heater may comprise an internal electric heating element for at least partially inserting into the aerosol-forming substrate of the smoking article. An "internal heating element" is one which is suitable for insertion into an aerosol-forming material. The invention is particularly advantageous when used in conjunction with an internal heating element since, in that case, there may be a tendency for the aerosol-forming substrate to stick to the heating element and therefore to break up as the aerosol-forming substrate is separated from the heating element.

The electric heater may comprise a single heating element. Alternatively, the electric heater may comprise more than one heating element. The heating element or heating elements may be arranged appropriately so as to most effectively heat the aerosol-forming substrate.

The electric heater may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Alternatively, the electric heater may comprise an infra-red heating element, a photonic source, or an inductive heating element.

The electric heater may take any suitable form. For example, the electric heater may take the form of a heating blade. Alternatively, the electric heater may take the form of a casing or substrate having different electro-conductive portions, or an electrically resistive metallic tube. Alternatively, one or more heating needles or rods that run through the centre of the aerosol-forming substrate may be as already described. Alternatively, the electric heater may be a disk (end) heater or a combination of a disk heater with heating needles or rods. Other alternatives include a heating wire or filament, for example a Ni—Cr (Nickel-Chromium), platinum, tungsten or alloy wire or a heating plate. Optionally, the heating element may be deposited in or on a rigid carrier material.

The electric heater may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. In one embodiment, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The electric heater may heat the aerosol-forming substrate by means of conduction. The electric heater may be at least partially in contact with the substrate, or the carrier on which the substrate is deposited. Alternatively, the heat from the electric heater may be conducted to the substrate by means of a heat conductive element.

Alternatively, the electric heater may transfer heat to the incoming ambient air that is drawn through the electrically heated smoking system during use, which in turn heats the aerosol-forming substrate by convection. The ambient air may be heated before passing through the aerosol-forming substrate.

In one embodiment, electric energy is supplied to the electric heater until the heating element or elements of the electric heater reach a temperature of between approximately 250° C. and 440° C. Any suitable temperature sensor and control circuitry may be used in order to control heating of the heating element or elements to reach the temperature of between approximately 250° C. and 440° C. This is in contrast to conventional cigarettes in which the combustion of tobacco and cigarette wrapper may reach 800° C.

In one embodiment, the extractor comprises gripping means for gripping the smoking article when the smoking article is received in the extractor.

The gripping means may ensure that the smoking article is correctly positioned so that the heater can heat the aerosol-forming substrate of the smoking article when the user puffs. In addition, the gripping means ensure that the smoking article does not fall out of the aerosol-generating device if the smoking system is oriented away from the vertical or away from the operating orientation. The gripping means may be arranged to grip the smoking article when a smoking article is received in the extractor, whether the extractor is in the first position or in the second position. Alternatively, the gripping means may be arranged to grip the smoking article when a smoking article is received in the extractor only when the sliding receptacle is in the first position.

As mentioned above, removal of the smoking article from the aerosol-generating device may be achieved in two phases. In the first phase, the smoking article and extractor are moved, preferably by sliding, relative to components of the aerosol-generating device. In the second phase, the smoking article, now separate from the heater, can be removed from the extractor. A gripping means, if present, may be arranged to release the smoking article during the second phase.

In one embodiment, the aerosol-generating device further comprises moving means for moving the extractor between the first and second positions.

The moving means may comprise motorised moving means. The extractor may be moved between the first and second positions automatically when the user exerts a force on the smoking article to remove the smoking article from the aerosol-generating device. Alternatively, the extractor may be moved between the first and second positions automatically when the user operates a switch. Alternatively, no moving means may be provided and the extractor may be moved between the first and second positions manually by a user.

During operation, the smoking article containing the aerosol-forming substrate may be completely contained within the aerosol-generating device. In that case, a user may puff on a mouthpiece of the aerosol-generating device.

Alternatively, during operation the smoking article containing the aerosol-forming substrate may be partially contained within the aerosol-generating device. In that case, the user may puff directly on the smoking article.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length. The aerosol-forming substrate may be received in the extractor of the aerosol-generating device such that the length of the aerosol-forming substrate is substantially parallel to the airflow direction in the aerosol-generating device.

The smoking article may have a total length between approximately 30 mm and approximately 100 mm. The smoking article may have an external diameter between approximately 5 mm and approximately 12 mm, for example about 7 mm. The smoking article may comprise a filter plug. The filter plug may be located at the downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Although reference is made to solid aerosol-forming substrates above, it will be clear to one of ordinary skill in the art that other forms of aerosol-forming substrate may be included in other embodiments of the invention. For example, the aerosol-forming substrate may be a liquid aerosol-forming substrate. If a liquid aerosol-forming substrate is provided, the aerosol-generating device preferably comprises means for retaining the liquid. For example, the liquid aerosol-forming substrate may be retained in a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic. The liquid aerosol-forming substrate may be retained in the porous carrier material prior to use of the aerosol-generating device or alternatively, the liquid aerosol-forming substrate material may be released into the porous carrier material during, or immediately prior to use. For example, the liquid aerosol-forming substrate may be provided in a capsule. The shell of the capsule preferably melts upon heating and releases the liquid aerosol-forming substrate into the porous carrier material. The capsule may optionally contain a solid in combination with the liquid.

Alternatively, the carrier may be a non-woven fabric or fibre bundle into which tobacco components have been incorporated. The non-woven fabric or fibre bundle may comprise, for example, carbon fibres, natural cellulose fibres, or cellulose derivative fibres.

Where the aerosol-generating device is an electrically heated smoking system, the electrically heated smoking system may further comprise a power supply for supplying power to the electric heater. The power supply may be any suitable power supply, for example a DC voltage source. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate or a Lithium-Polymer battery.

The electrically heated smoking system may further comprise electronic circuitry arranged to be connected to the power supply and the electric heater. If more than one heating element is provided, the electronic circuitry may provide for the heating elements to be independently controllable. The electronic circuitry may be programmable.

In one embodiment, the aerosol-generating device further comprises a sensor to detect air flow indicative of a user taking a puff which enables puff based activation of the electric heater or an improved energy management of the electric heater. The sensor may be any of: a mechanical device, an electro-mechanical device, an optical device, an opto-mechanical device and a micro electro-mechanical systems (MEMS) based sensor. In that embodiment, the sensor may be connected to the power supply and the system is arranged to activate the electric heater when the sensor senses a user taking a puff. In an alternative embodiment, the system further comprises a manually operable switch, for a user to initiate a puff or to enable a long-lasting smoking experience.

Specific embodiments will now be described, by way of example only, with reference to the accompanying drawings, in which.

Figure 9:
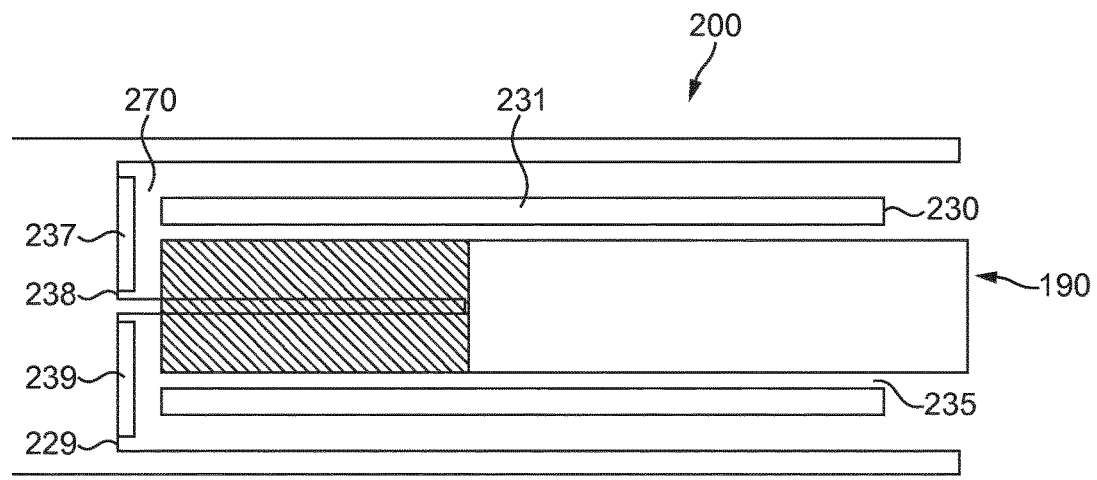
Figure 10:
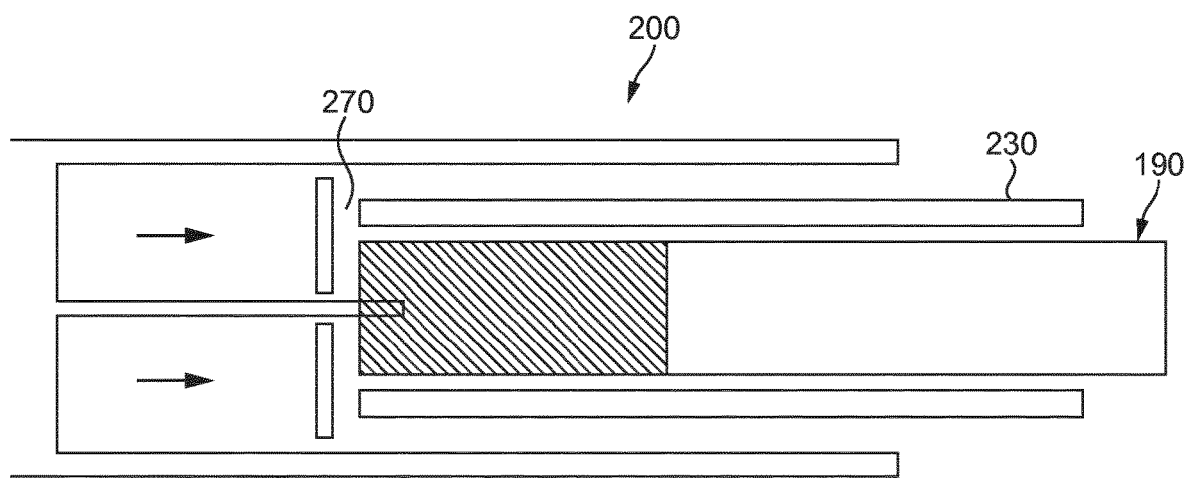

FIG. 9 is a schematic cross-sectional diagram showing a portion of an aerosol-generating device according to one embodiment of the invention, the aerosol-generating device being engaged with an aerosol-generating article in an operating position; and FIG. 10 is a schematic diagram of the aerosol-generating device and aerosol-generating article of FIG. 9 with its extractor in an extraction position.

Figure 1:
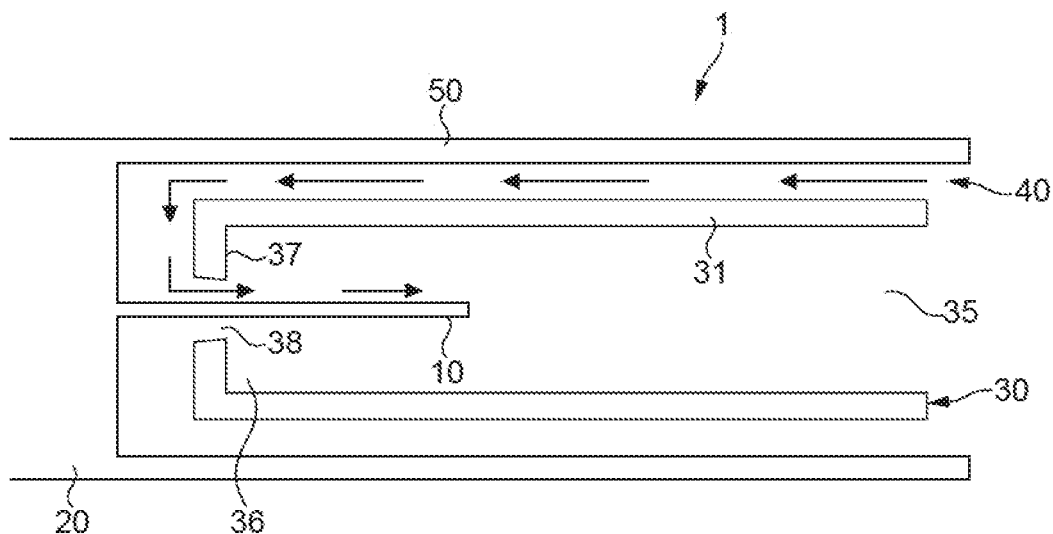
FIG. 1 is a schematic cross-sectional diagram of a portion of a prior art aerosol-generating device showing, in particular, a heater, an extractor, and an air-flow path into the device.

FIG. 1 illustrates a portion of a prior art aerosol-generating device that includes an extractor of the type disclosed, for example, in WO 2013/076098. The device 1 includes a heater blade 10 mounted by and projecting outwardly from a heater support 20. The device 1 further includes an extractor 30 that is slideably mounted such that it can move relative to the heater 10. The extractor 30 has a cavity 35 for receiving an aerosol-generating article. A proximal end of the cavity is open to allow an aerosol-generating article to be received. A distal end of the cavity 36 terminates in an end-wall 37 which acts to support a distal end of an aerosol-generating article received in the cavity 35. An aperture 38 defined through the thickness of the end-wall 37 of the extractor 30 allows the heater blade 10 to penetrate into the cavity 35.

FIG. 1 illustrates the extractor in a first, or operating, position relative to the heater blade. In this position an aerosol-generating article received in the cavity 35 can be penetrated by the heater blade 10, thereby allowing the heater blade 10 to heat an aerosol-forming substrate of the aerosol-generating article. An air-flow path 40 is defined by channels extending between external walls of the aerosol-generating device 50 and side walls 31 of the extractor. The arrows on FIG. 1 illustrate the air-flow path as it passes along a channel between side walls 50 of the device and side walls 31 of the extractor before changing direction to flow between the heater support 20 and the distal end-wall 37 of the extractor, and then finally changing direction again to flow through the aperture 38 of the end-wall and into the cavity 35. This air flow passes in proximity to the heater and the air may therefore be heated and contribute to the formation of an aerosol.

The aerosol-generating articles are preferably smoking articles comprising tobacco. As successive aerosol-generating articles are consumed, fragments of aerosol-forming substrate and other debris and residue derived from the aerosol-forming substrate adhere to the heater blade and deposit thereon. Some of this debris and residue passes through the aperture 38 at the distal end-wall 37 of the extractor and collects in a gap 21 defined between the heater support 20 and the distal end-wall 37 of the extractor. This gap exists to allow air flow to the aperture 38 and consequently into the cavity.

Figure 2:
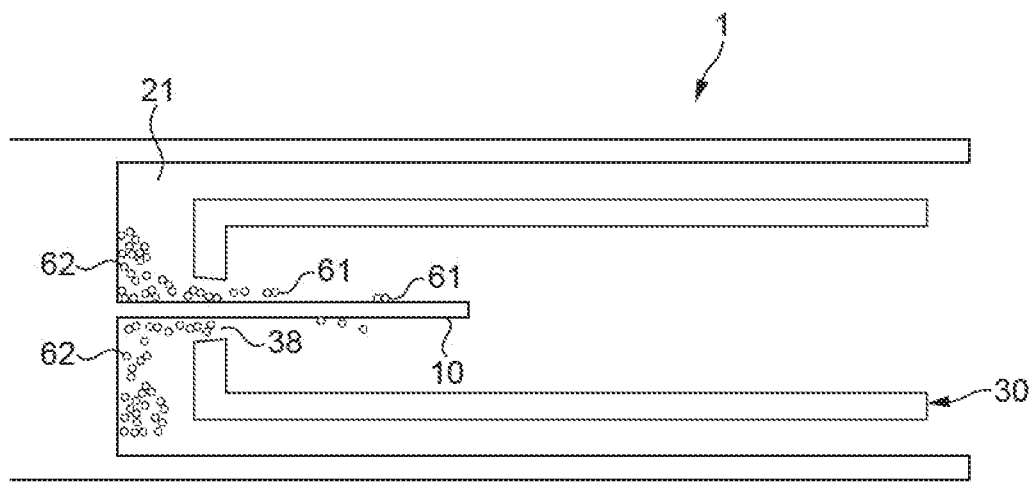
FIG. 2 is a schematic diagram of the prior art aerosol-generating device as illustrated in FIG. 1, showing the positions that tobacco debris and residues typically build up within the device.

Tests have been carried out to determine the level of substrate-derived debris and residue collected in the device with repeated usage. FIG. 2 illustrates a typical build up of such residue as occurs after about forty aerosol-generating articles have been consumed using the device. As can be seen in the schematic illustration of FIG. 2, some debris and residue 61 adheres to the heater blade 10, while other debris and residue 62 accumulates in the gap 21 between the heater support and the extractor and within the aperture 38 defined into the extractor. In addition to contributing to the formation of undesirable aerosol products and odours, this residue and debris also affects the air flow into the device and, therefore, affects the formation of aerosol over time. As the debris and residue 61, 62 forms on the blade and builds up around the base of the blade it becomes difficult to clean the debris effectively. The debris and residue is highly adherent and resists light mechanical brushing. A more vigorous mechanical brushing is undesirable as it is easy to damage the heater blade 10. The debris 62 mainly builds up at the base of the heater blade 10 and, as this portion of the heater blade tends to be unheated or heated to a lower temperature than a working end of the heater blade, it is difficult to remove using pyrolysis. That is, it is difficult to remove debris and residue building up around the base of a heater blade by heating the heater blade to a high temperature in order to pyrolyse the residue and debris, because this portion of the heater blade needs to be maintained at a low temperature. Furthermore, the portion of the device that collects the debris is the portion of the aerosol-generating device that includes electronics. It is, therefore, difficult to wash this portion of the device without risking damage to the electronics.

Figure 3:
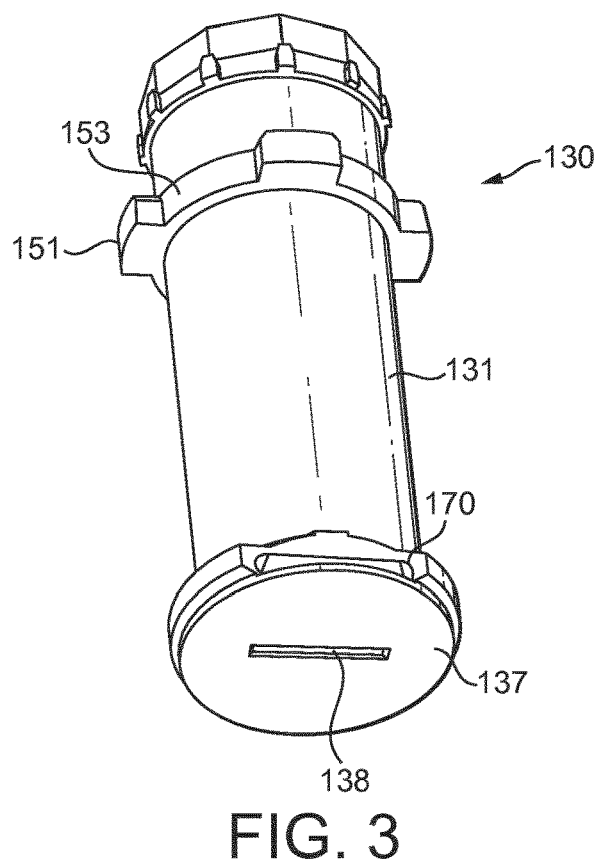
FIG. 3 is a perspective view of an extractor for use in an aerosol-generating device according to one embodiment of the invention.
Figure 4:
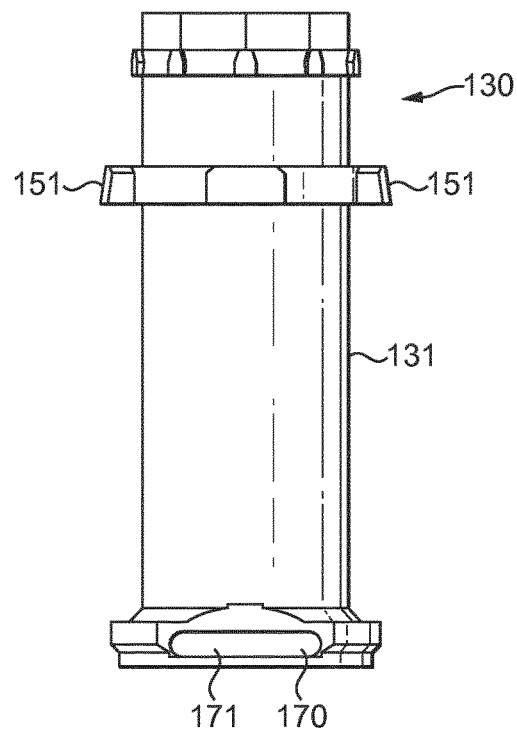
FIG. 4 is a side view of the extractor of FIG. 3.

FIGS. 3 and 4 are a perspective illustration and a side illustration respectively of an extractor 130 for an aerosol-generating device. The extractor is a substantially tubular structure having a tubular side wall 131 defining a cavity (not shown) for receiving an aerosol-generating article, a distal end of the cavity terminating in an end-wall 137. A slot-shaped aperture 138 is defined through the end-wall 137 to allow a heater blade to penetrate the cavity of the extractor 130. The outer surface of the end-wall 137 is designed to fit flush against a corresponding surface of a heater support without leaving a gap. The extractor 130 includes an orientation ring 153 comprising a plurality of orientation lugs 151. The orientation lugs engage with corresponding grooves on a portion of the aerosol-generating device in order to appropriately orient the extractor 130 and the aperture 138 so that it engages with a heater blade.

An air inlet 170 of an air-flow channel 171 is defined in a side wall 131 of the extractor 130. The air-flow channel 171 allows flow of air into the cavity. The arrangement of the air-flow channel 171 may be more clearly seen in the schematic diagrams of FIGS. 5 and 6.

Figure 5:
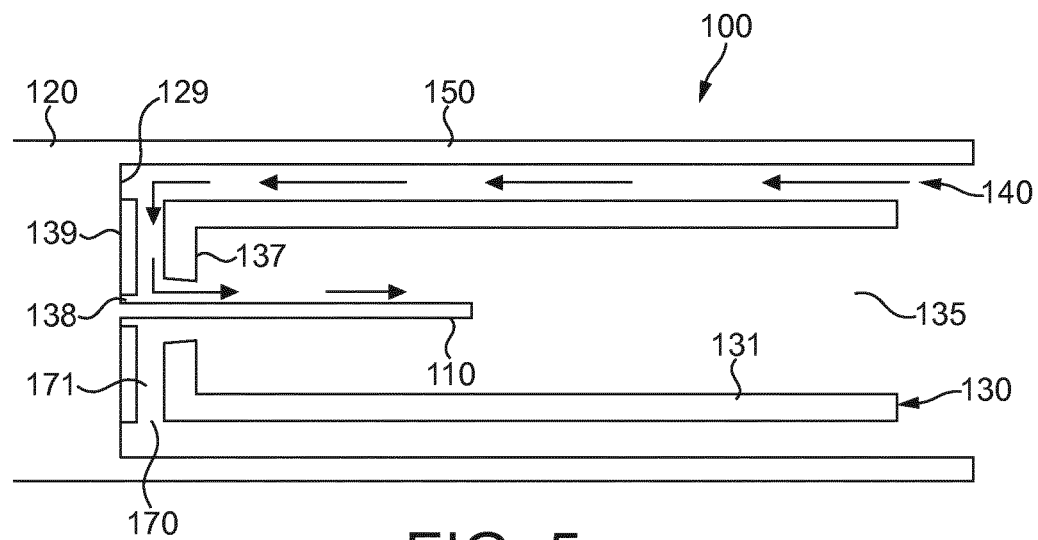
FIG. 5 is a schematic cross-sectional diagram of a portion of an aerosol-generating device according to one embodiment of the invention, showing in particular a heater, an extractor, and an air-flow path into the device.

The aerosol-generating device 100 of FIG. 5 is a schematic cross-sectional diagram. The device 100 includes a heater blade 110 mounted by and extending from a heater support 120. The device 100 further includes an extractor 130 of the type illustrated in FIGS. 3 and 4. The extractor defines a cavity 135 for receiving an aerosol-generating article. The cavity is defined by side walls 131 and by an end-wall 137. An aperture 138 is defined through the end-wall 137 to allow passage of the heater 110 into the cavity 135. An outer face 139 of the end-wall 137 is planar and abuts a planar face 129 of the heater support 120. There is substantially no gap between the outer face 139 or the end-wall 137 and the face 129 of the heater support 120. The air-flow channel 171 is defined as a radially extending channel within the thickness of the end-wall 137. The inlet 170 of the air-flow channel 171 is defined in side wall 131 of the extractor. The air-flow channel 171 extends radially inwards towards the heater blade aperture. The air-flow channel 171 joins the aperture 138, thereby allowing air flow into the cavity 135 of the extractor 130. An air-flow path is shown by arrows in FIG. 5. The arrows show that an air-flow path 140 is defined between an outer wall 150 of the device 100 and side walls 131 of the extractor. The air flow path then deviates through the air-flow inlet 170 defined in a side wall 131 of the extractor, along an air-flow channel 171 defined within the end-wall 137 of the extractor, and into the cavity 135 of the extractor by means of the aperture 138 through which the heater 110 extends.

Figure 6:
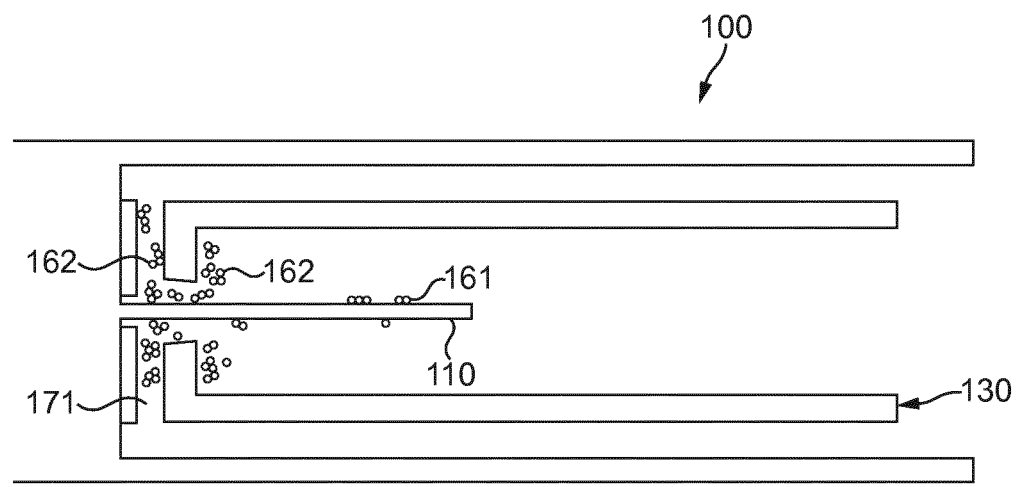
FIG. 6 is a schematic diagram of the aerosol-generating device shown in FIG. 5, showing the positions that tobacco debris and residues typically build up within the device.

FIG. 6 shows a typical build-up of residue after use. The residue 161, 162 may form extensively within the air-flow channel 171. As the majority of the debris and residue 162 is retained within the extractor 130, it is easy to keep the device clean. For example, the extractor 130 may be removed from the device 100 and washed in running water to remove the debris and residue. This provides a convenient way of keeping the internal portions of the device clean. Furthermore, the aperture 138 through which the heater blade 110 extends may be dimensioned tightly, at least for a portion of the aperture, so that the heater blade 110 only just passes through the aperture. The aperture may be dimensioned such that the heater blade physically engages with the extractor on passing through the aperture 138. Thus, the aperture may be dimensioned such that the heater blade is scraped or wiped when the extractor is moved from its operating position to the extraction position, thereby cleaning the blade of debris and residue, the debris and residue remaining within the extractor.

Thus, by moving the air-flow inlet 170 to a position that is radially external to the aperture 138 it is possible to configure the device such that debris and residue is substantially retained within the extractor. This keeps the heater blade and the device relatively clean. The debris and residue within the extractor may be easily and conveniently cleaned by washing the extractor. The invention makes it much simpler to maintain cleanliness of the device and, therefore improves the user experience of the device.

Figure 7:
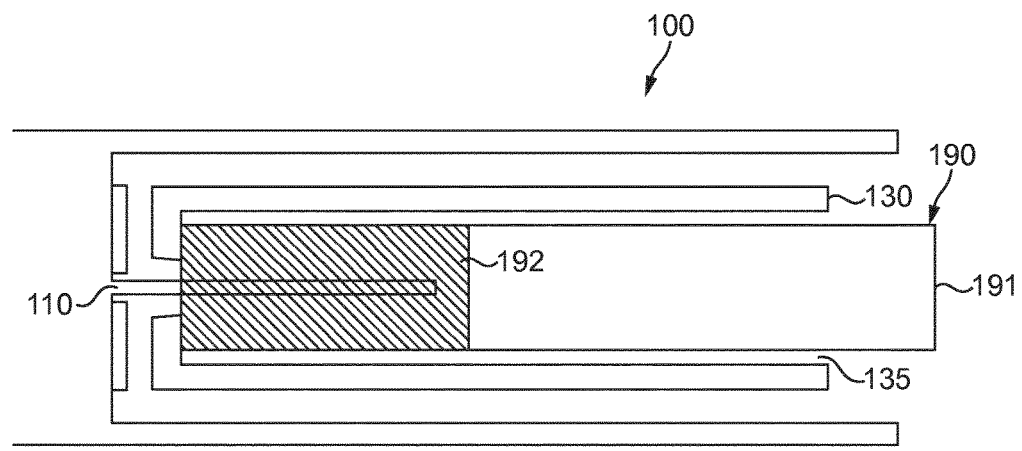
FIG. 7 is a schematic diagram showing the aerosol-generating device of FIG. 5 when engaged with an aerosol-generating article.
Figure 8:
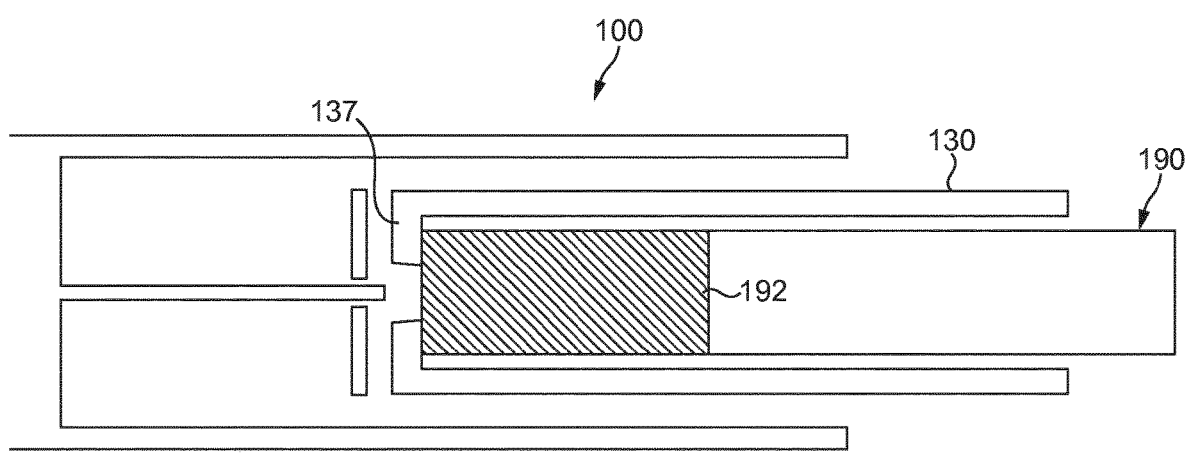
FIG. 8 is a schematic diagram illustrating the aerosol-generating device and aerosol-generating article of FIG. 7 with its extractor arranged in an extraction position.

A method of operating the device 100 will now be described with reference to FIGS. 7 and 8. FIG. 7 illustrates the aerosol-generating device 100 of FIGS. 5 and 6 engaged with an aerosol-generating article 190. The aerosol-generating article 190 has a proximal, or mouth, end 191 on which a user may draw during use to obtain an aerosol. The aerosol-generating article 190 further comprises an aerosol-forming substrate 192 located towards a distal end of the article 190. In FIG. 7 the aerosol-generating article 190 is shown received within the cavity 135 of the extractor 130. The extractor is in its first position, or operating position, in which the aerosol-generating article 190 is penetrated by the heater 110. The heater is actuated to heat the aerosol-generating article. As the user draws on the proximal end of the aerosol-generating article, air is drawn into the aerosol-generating device and passes through the aerosol-forming substrate 192. Volatile components evolved from the aerosol-forming substrate are entrained within the air flow and condensed to form an inhalable aerosol.

Once the user has consumed the aerosol-generating article 190, the extractor 130 is moved to its second, extraction, position. In this position the end-wall 137 of the extractor engages with the aerosol-generating article and pulls the aerosol-generating article from the heater blade 110. The aerosol-generating article may then be removed from the cavity easily. Debris, such as fragments of tobacco are retained within the extractor.

After the aerosol-generating device has been used for a number of times, the build-up of debris and residue within the extractor may start to affect the air flow within the extractor. At this point the entire extractor 130 is removed from the aerosol-generating device and is cleaned by washing with water.

The aerosol-generating article 190 is preferably a smoking article and the aerosol-forming substrate is preferably a substrate comprising homogenised tobacco. In a preferred embodiment, the smoking article has an elongate cylindrical shape and comprises an aerosol-forming substrate, and a filter plug, arranged sequentially and in coaxial alignment. The aerosol-forming substrate and filter plug are over-wrapped with an outer paper wrapper. Other components may be included in the smoking article.

FIGS. 9 and 10 illustrate a further embodiment of an aerosol-generating device 200 engaged with an aerosol-generating article 190. As previously described the aerosol-generating device includes an extractor 230. The extractor has a cavity 235 defined by side walls 231 for receiving the aerosol-generating article 190. A distal end of the cavity 235 terminates in an end-wall 237. An aperture 238 is defined through the end-wall for allowing passage of a heater blade. When the extractor 230 is in its operating position, an outer face 239 of the end-wall 237 abuts a face 229 of the heater blade support. There is substantially no gap between the extractor and the heater support. An air-flow inlet 270 is defined through a side wall 231 of the extractor 230. In use, air passes into the cavity 235 through air inlets 270.

The difference between the embodiment of FIG. 9 and the embodiment of FIG. 5 is that air-flow inlets are defined through the side of the extractor and air flows directly through these inlets into the cavity. There may be grooves within the end-wall to channel the flow of air towards the heater blade, but there are no radially-extending channels defined within the end wall itself in this embodiment.

FIG. 10 shows the device 200 of FIG. 9 with the extractor 230 moving towards its second, extraction, position.

The invention claimed is:

1. An elongated aerosol-generating device configured to receive an aerosol-generating article, comprising:
   a heater extending longitudinally with respect to the elongated aerosol-generating device, and being configured to heat the aerosol-generating article and to penetrate an internal portion of the aerosol-generating article; and an extractor configured to extract the aerosol-forming article received in the aerosol-generating device, the extractor being movably coupled to the aerosol-generating device between an operating position and an extraction position, the operating position being defined by the heater being in contact with the aerosol-generating article, and the extraction position being defined by the heater being separated from the aerosol-generating article, the extractor comprising a cavity configured to receive the aerosol-generating article, a first aperture defined through an end-wall of the cavity and being configured to allow the heater to penetrate the cavity when the extractor is moved between the extraction position and the operating position, wherein the extractor further defines an air-flow channel configured to allow air flow into the cavity, an inlet of the air-flow channel being positioned radially-outward of the first aperture and in which an air-flow path through the extractor involves airflow in a radial direction toward the heater for at least a portion of the air-flow path, wherein an external surface of the end-wall is configured to fit flush against a corresponding surface of a heater support of the aerosol-generating device when the extractor is in the operating position, wherein the air-flow channel is disposed entirely within a thickness of the end-wall, and wherein:
  (a) the inlet of the air-flow channel is defined in a radially-outermost portion of the end-wall of the cavity and at least a portion of the air-flow channel extends radially within the end-wall between internal and external surfaces of the end-wall defined in a longitudinal direction, or
  (b) at least a portion of the air-flow channel extends radially within the end-wall of the cavity between the internal and the external surfaces of the end-wall defined in the longitudinal direction.

2. The elongated aerosol-generating device according to claim 1, wherein the first aperture is dimensioned to allow a clearance of 0.5 mm or less to the heater.

3. The elongated aerosol-generating device according to claim 1, wherein the first aperture and the air-flow channel are arranged so as to retain debris from the aerosol-generating article within the extractor when the aerosol-generating article has been extracted.

4. The elongated aerosol-generating device according to claim 1, wherein an outer face of the end-wall abuts a portion of the aerosol-generating device when the extractor is in the operating position such that debris from the aerosol-generating article cannot build up in the aerosol-generating device.

5. The elongated aerosol-generating device according to claim 1, wherein the extractor is configured to be removed from the aerosol-generating device.

6. The elongated aerosol-generating device according to claim 1, further comprising a first air-flow channel and a second air-flow channel, wherein inlets to the first air-flow channel and the second air-flow channel are located on opposite sides of the extractor.

7. An aerosol-generating system, comprising:
an aerosol-generating article, comprising an aerosol-forming substrate configured to evolve an inhalable aerosol when heated; and
an elongated aerosol-generating device, comprising:
  a heater extending longitudinally with respect to the aerosol-generating device, and being configured to heat the aerosol-generating article and to penetrate an internal portion of the aerosol-generating article; and
  an extractor configured to extract the aerosol-forming article received in the aerosol-generating device, the extractor being movably coupled to the aerosol-generating device between an operating position and an extraction position, the operating position being defined by the heater being in contact with the aerosol-generating article, and the extraction position being defined by the heater being separated from the aerosol-generating article,
  the extractor comprising a cavity configured to receive the aerosol-generating article, a first aperture defined through an end-wall of the cavity and being configured to allow the heater to penetrate the cavity when the extractor is moved between the extraction position and the operating position,
  wherein the extractor further defines an air-flow channel configured to allow air flow into the cavity, an inlet of the air-flow channel being positioned radially-outward of the first aperture and in which an air-flow path through the extractor involves airflow in a radial direction toward the heater for at least a portion of the air-flow path,
  wherein an external surface of the end-wall is configured to fit flush against a corresponding surface of a heater support of the aerosol-generating device when the extractor is in the operating position,
wherein the air-flow channel is disposed entirely within a thickness of the end-wall, and
wherein:
  (a) the inlet of the air-flow channel is defined in a radially-outermost portion of the end-wall of the cavity and at least a portion of the air-flow channel extends radially within the end-wall between internal and external surfaces of the end-wall defined in a longitudinal direction, or
  (b) at least a portion of the air-flow channel extends radially within the end-wall of the cavity between the internal and the external surfaces of the end-wall defined in the longitudinal direction.

8. The aerosol-generating system according to claim 7, wherein the aerosol-forming substrate comprises a sheet of homogenised tobacco.

* * * * *